US012749568B2

(12) United States Patent
Srivathsa et al.

(10) Patent No.: US 12,749,568 B2
(45) Date of Patent: Sep. 29, 2026

(54) INTELLIGENT DISPLAY CORRIDOR LIGHT

(71) Applicant: Rauland-Borg Corporation, Mount Prospect, IL (US)

(72) Inventors: Karthik Srivathsa, Palatine, IL (US); Carl Renaghan, Elmhurst, IL (US); Paul Chartouni, Mount Prospect, IL (US); Patrick Fitzgerald, Arlington Heights, IL (US); Gina Pampalone Brody, Mount Prospect, IL (US)

(73) Assignee: RAULAND-BORG CORPORATION, Mount Prospect, IL (US)

( * ) Notice: Subject to any disclaimer, the term of this patent is extended or adjusted under 35 U.S.C. 154(b) by 0 days.

(21) Appl. No.: 18/648,664

(22) Filed: Apr. 29, 2024

(65) Prior Publication Data

US 2025/0336506 A1 Oct. 30, 2025

(51) Int. Cl.
*G16H 40/20* (2018.01)
*G06F 3/14* (2006.01)

(52) U.S. Cl.
CPC ........... *G16H 40/20* (2018.01); *G06F 3/1431* (2013.01)

(58) Field of Classification Search
None
See application file for complete search history.

(56) References Cited

U.S. PATENT DOCUMENTS

| | | | | |
|---|---|---|---|---|
| 2004/0138925 | A1* | 7/2004 | Zheng | G06Q 10/10 705/2 |
| 2014/0266642 | A1* | 9/2014 | Girardeau | G06Q 10/063114 340/286.07 |
| 2018/0050226 | A1* | 2/2018 | Park | G09F 27/00 |
| 2019/0172578 | A1* | 6/2019 | Zuckerman | G16H 40/20 |
| 2022/0051532 | A1* | 2/2022 | Hatch | G08B 5/36 |
| 2022/0122724 | A1* | 4/2022 | Durlach | A61B 5/002 |

* cited by examiner

*Primary Examiner* — Joseph R Haley
(74) *Attorney, Agent, or Firm* — Leydig, Voit & Mayer, Ltd.

(57) ABSTRACT

A corridor display unit is configured for mounting to a surface of a corridor in a hospital or health care facility. The corridor display unit includes one or more flat panel displays and a mounting frame that outlines and encloses the flat panel display. To annunciate information about patient status or location status to caregivers, the flat panel display can display an annunciation image rendered from image files that may include a textual component and a graphical component. The annunciation image may also include real-time data and prerecorded data about the patient status or the location status.

22 Claims, 11 Drawing Sheets

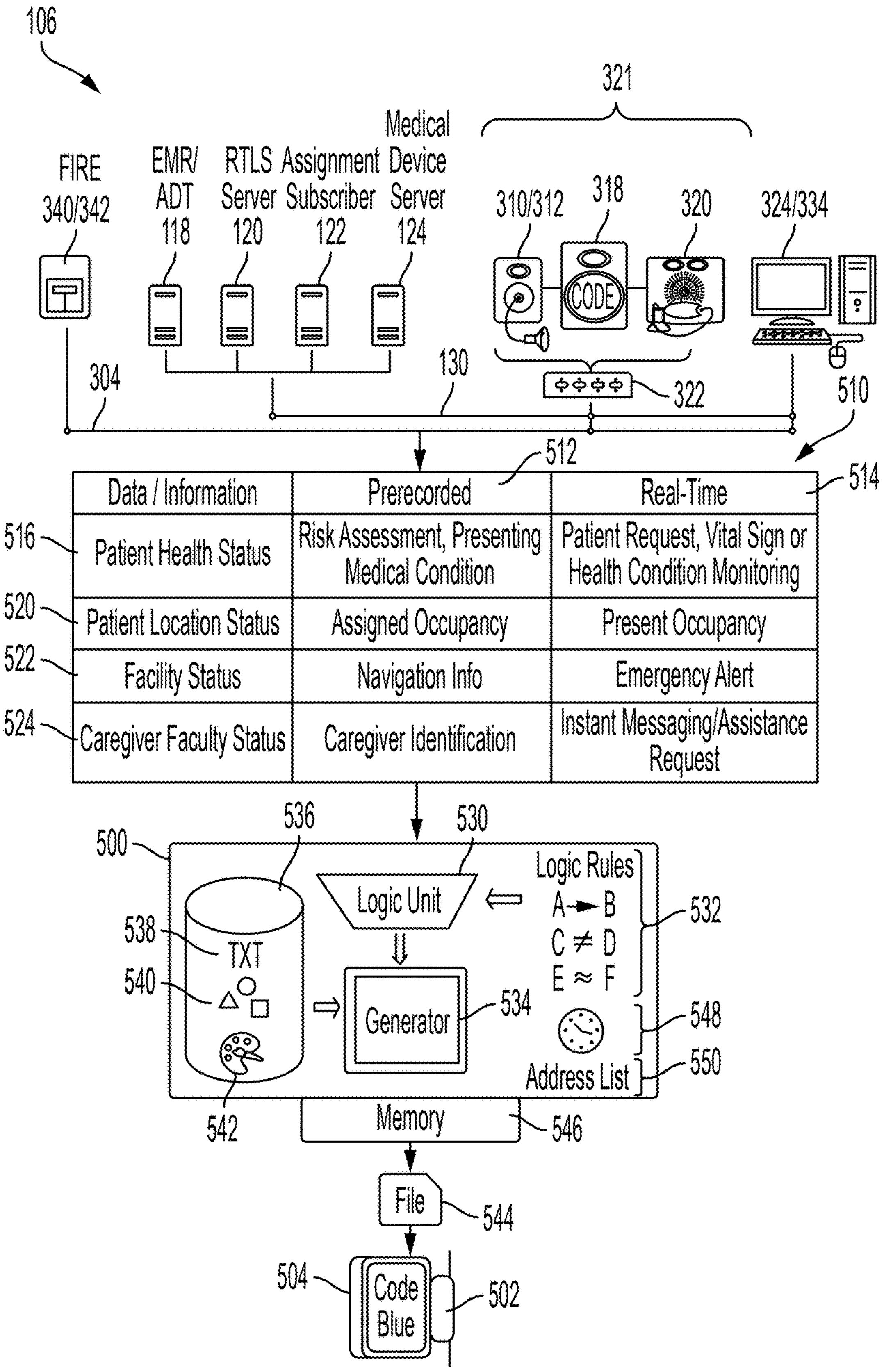

| Data / Information | Prerecorded | Real-Time |
|---|---|---|
| Patient Health Status | Risk Assessment, Presenting Medical Condition | Patient Request, Vital Sign or Health Condition Monitoring |
| Patient Location Status | Assigned Occupancy | Present Occupancy |
| Facility Status | Navigation Info | Emergency Alert |
| Caregiver Faculty Status | Caregiver Identification | Instant Messaging/Assistance Request |

FIG. 5

INTELLIGENT DISPLAY CORRIDOR LIGHT

BACKGROUND OF THE INVENTION

Typically, a hospital includes various units that service patients of the hospital. A non-exhaustive list of units within a hospital may include: an Intensive Care Unit (ICU), a medical/surgery unit, a maternity ward, and an Emergency Department (ED). Further, each unit within the hospital typically includes a variety of patient rooms or other locations where a patient may be present during the medical visit. The various patient locations are interconnected by hallways, corridors, or structural passages in the building housing the hospital.

To communicate announcements and messages about the patient to the caregivers located in the corridors, signaling devices traditionally in the form of color-coded corridor lights are mounted in the corridors proximate to the entrance to the patient location or proximate to a caregiver station. An example of a corridor light is provided in U.S. Pat. No. 6,693,514 which describes a plurality of LED lights that are mounted vertically to a light fixture on the corridor wall. The color coded sequence of lights correspond with predetermined definitions and meanings that the caregivers and other staff are trained to recognize and understand.

A hospital typically employs many caregivers and other staff tasked with providing specific and designed services to the patients. Typically, these caregivers are both highly skilled and trained to provide a specific service for the patients. Effective and efficient patient service and care requires solid communication and cooperative action between caregivers, staff and patients. The color coded corridor lights facilitate patient-caregiver communication. However, expansive developments in telecommunications have vastly increased the amount and accessibility to information including in a hospital or healthcare facility setting.

In view of the above, hospitals typically make use of complicated administrative systems embodied as enterprise-wide computer-based network applications to monitor and track information such as the condition of the patients, activities of the caregivers, status or condition of patient locations or hospital equipment, etc. To accomplish these tasks, the hospital network system relies upon information and data input to the system, which is processed by various computer executable applications or programs and the resulting output is communicated to the caregivers and other individuals in various different forms. The present disclosure is directed to an arrangement and method for facilitating the communication and annunciation of information within a hospital environment via a computerized hospital networks system.

BRIEF SUMMARY OF THE INVENTION

The disclosure is directed to a corridor display unit that can be mounted proximate to a patient location in a hospital or healthcare facility that is configured to display contextual annunciation images for conveying data and information to caregivers. The corridor display unit can be intended to replace traditional corridor lights that are typically mounted above the entrance to a patient location and/or at corridor intersections for visible exposure to staff and caregivers. The contextual annunciation images include data and information about the patient health status, patient location status (e.g. whether occupied or unoccupied and occupant identification or title), facility status, and/or caregiver status. Data may refer to basic facts and details and information may refer to the contextual representation of the data presented in a manner to facility understanding and comprehensibility of the data. The corridor display unit can be associated with a display controller configured to collect, select, supplement, and organize the data for generating informative and contextual annunciation images on the corridor display units. The contextual annunciation images can include or represent the collected data, along with data from possibly other sources, and present it in a meaningful manner in relation to the location or audience.

In an aspect, the disclosure provides a hospital network system including a plurality of corridor display units associated with patient locations in a hospital or healthcare facility. The corridor display units include a flat panel display disposed in a mounting frame that is adapted for mounting to a corridor surface proximate the patient location. Each corridor display unit is associated with a display controller that is configured to generate annunciation images having textual components and graphical components for rendering a contextual annunciation image on the flat panel display. The textual components and graphical components of the contextual annunciation images are associated with data input to the display controller.

The disclosure further describes a corridor display unit for annunciating information within a corridor of a hospital or health facility. The corridor display unit includes at least one flat panel display for displaying a contextual annunciation image having a textual component and a graphical component. The flat panel display is located in a mounting frame for mounting the corridor display unit to a corridor surface. The mounting frame thus outlines and encloses the flat panel display. The corridor display unit is operatively associated with a display controller programmed to generate an image file for rendering the contextual annunciation image on the flat panel display.

In another aspect, the disclosure provides a hospital network system including a corridor display unit associated with a patient location. The corridor display unit has a flat panel display disposed in a mounting frame for mounting to a corridor surface proximate the patient location. The corridor display unit is networked with a display controller programmed to generate an image file corresponding to a contextual annunciation image for rendering on the flat panel display. To improve comprehensibility, the contextual annunciation image can have a textual component and a graphical component. To provide patient status data for generating and inclusion in the contextual annunciation image, the display controller is communicatively networked with an electronic medical record server storing one or more patient electronic medical records. The display controller is also communicatively networked with a caregiver call system including one or more call devices for communicating patient status data for generating and inclusion in the contextual annunciation image.

A possible advantage of the disclosure is that the corridor display units can present contextual annunciation images conveying patient health care data and the like in an informative and comprehensible manner for caregivers and other intended individuals. A related advantage is that the contextual annunciation images displayed on the corridor display units reduces the training and effort required by caregivers to interpret and understand the data displayed on the corridor display units. Relatedly, the contextual annunciation images can include graphical components and symbols that may be language independent furthering comprehensibly among caregivers. The corridor display units and contextual annunciation images displayed thereon can include data and information from a greater number of different sources than traditional color-coded corridor lights. These and other possible features and advantages of the disclosure will be apparent from the following detailed description and the accompanying figures.

BRIEF DESCRIPTION OF THE SEVERAL VIEWS OF THE DRAWINGS

FIG. 5 is a schematic diagram of a display controller communicatively networked with other systems and computing devices in a hospital or healthcare system for the generation of contextual annunciation images for display on the corridor display units.

DETAILED DESCRIPTION OF THE DRAWINGS

Figure 1:
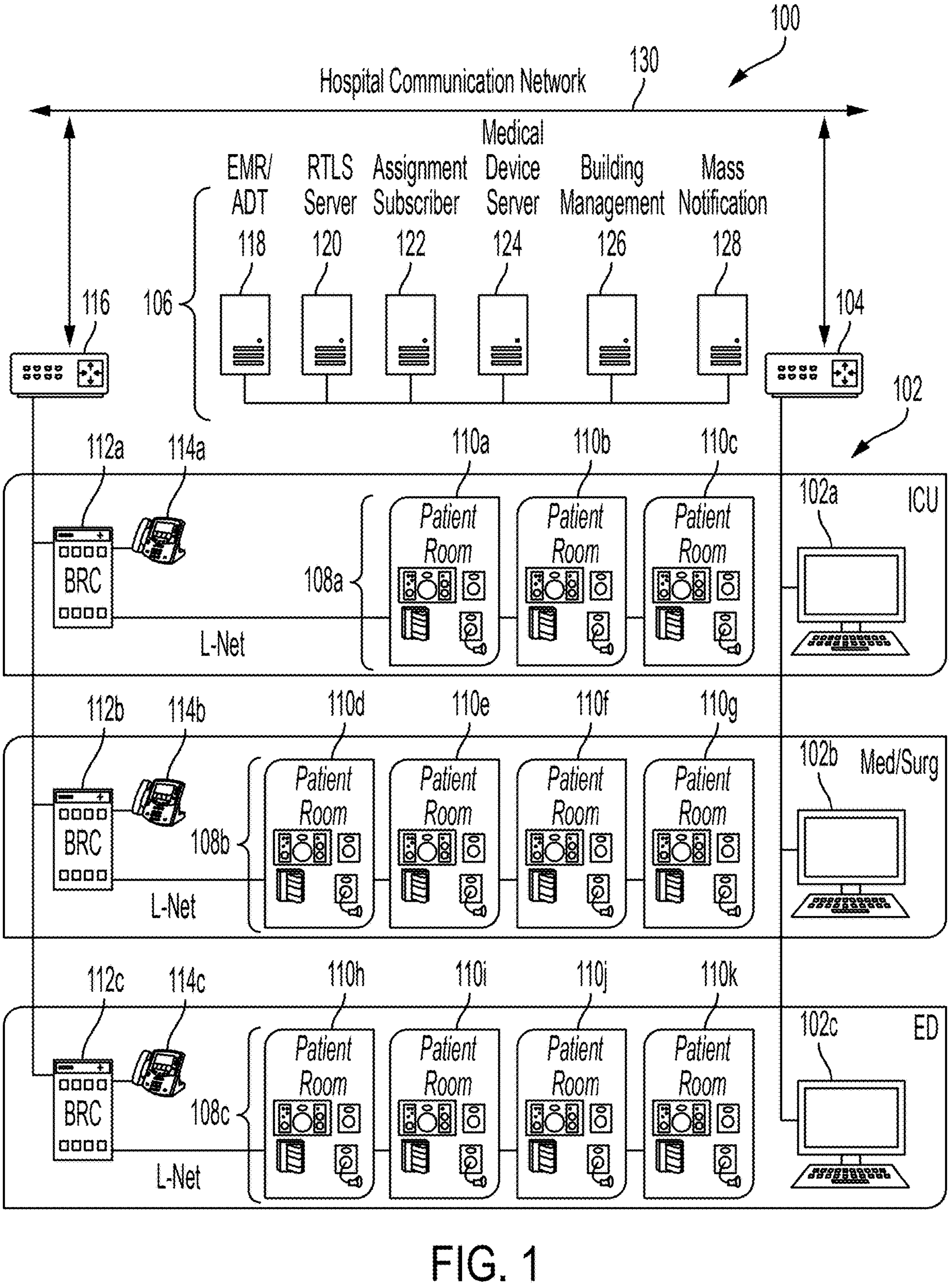
FIG. 1 illustrates a hospital or healthcare communication system communicatively interconnecting devices and resources in a plurality of patient rooms or locations in accordance with an embodiment of the disclosure.

FIG. 1 illustrates an exemplary, enterprise wide, computer-based computer hospital network system 100 for enabling information technology and communication services in a hospital or healthcare environment. The hospital network system 100 may be associated with a plurality of hospital units 102, including for example an Intensive Care Unit (ICU) 102*a*, a medical/surgery unit 102*b*, and an Emergency Department (ED) 102*c*. In an embodiment, each of the hospital units 102 may be associated with client computing devices 102*a*-102*c* located in the hospital unit and that are operatively associated with one or more peripheral client input devices, monitors, sensors, etc. Each of the client computing devices 102*a*-102*c* in the hospital units 102 are networked via a router 104 with one or more network servers 106 that exchange information with and provides functionality for the plurality of client computing devices 102*a*-102*c* associated with the hospital units 102. The network servers 106 can be responsible for managing data communication, notification alerts, activities scheduling, etc. for each of the hospital units 102.

Each hospital unit 102*a*, 102*b*, and 102*c* includes respective patient locations 108*a*, 108*b*, and 108*c* such as patient rooms. The patient locations 108*a*, 108*b*, and 108*c* may be traditional enclosed spaces bounded by a number of walls for examination or other medical procedures or may be intended for patient recovery and monitoring after a medical procedure. In other embodiments, the patient locations 108*a*, 108*b*, and 108*c* may be partitioned or separated using temporary dividers such as curtains, or may be isolated healthcare pods. The patient locations 108*a*, 108*b*, and 108*c* may include a plurality of nurse call devices 110*a*-110*k*. Examples of nurse call devices 110*a*-110*k* include call devices such as pull cord stations or pushbutton stations, corridor lights, and data input terminals. As shown in the illustrated embodiment, the nurse call devices 110*a*-110*k* may be the same in each patient room. However, in other embodiments, nurse call devices 110*a*-110*k* can include different equipment in each room and is dependent on a hospital's preferred installation.

Each hospital unit 102*a*, 102*b*, and 102*c* also includes a respective administrative console 114*a*, 114*b*, and 114*c*. The administrative consoles 114*a*, 114*b*, and 114*c* provide a centralized area where administrative functions are performed by an administrator for each of the hospital units 102*a*, 102*b*, and 102*c*, respectively. The administrative consoles 114*a*, 114*b*, and 114*c* may be operatively associated with the client computer devices 102*a*, 102*b*, 102*c* that are associated with each of the hospital units 102*a*, 102*b*, 102*c*. The administrative consoles 114*a*, 114*b*, and 114*c* and the client computer devices 102*a*, 102*b*, 102*c* may cooperate to function as data input terminals to input patient specific information, caregiver information, and/or location specific information. For each hospital unit 102*a*, 102*b*, and 102*c*, the administrative consoles 114*a*, 114*b*, and 114*c* along with the nurse call equipment 110*a*-110*k* are connected to a router 116 via Branch Regional Controllers (BRCs) 112*a*, 112*b*, and 112*c*. The router 116 networks the administrative consoles 114*a*, 114*b*, and 114*c* along with the nurse call equipment 110*a*-110*k* to the nurse call and caregiver Assignment Scheduler server 122 that may be among the plurality of network servers 106. The routers 104, 116 can be communicatively coupled to and exchange information and data with each of the plurality of network servers 106.

The network servers 106 can include further sub-servers including an Electronic Medical Records/Admission/Discharge/Transfer (EMR/ADT) server 118, a Real Time Location System (RTLS) server 120, an Assignment Scheduler server 122, a Medical Device server 124, a building management server 126, and a mass notification server 128. The EMR/ADT server 118 keeps and provides access to medical records of patients within the hospital for caregivers to review and/or update those records accordingly. The EMR/ADT server 118 can electronically maintain and edit a patient's electronic medical record (EMR), which refers to the stored record of the patient's medical and clinical healthcare history, or a similar patient health record.

The RTLS server 120 enables an RTLS system within the hospital that tracks individual caregiver locations such that the RTLS server 120 can provide a location of any individual caregiver at any time while that caregiver is in the hospital. RTLS systems use wireless tags or badges that are carried by caregivers or attached to objects that move throughout the hospital or healthcare facility and that can be sensed or detected when in proximity with wireless sensors or receivers that are disposed at fixed locations throughout the hospital or healthcare facility. The RTLS system can use any suitable short-range communication protocol such as Bluetooth connectivity.

The Assignment Scheduler server 122 maintains and updates a schedule of activities or actions that may be assigned to the caregivers or associated with the patients. The Assignment Scheduler server 122 can maintain an electronic table listing the patient locations throughout the hospital or facility, the patient assignments to the various patient locations, and the caregiver and staff assignments with respect to the patients and patient locations.

The Medical Device server 124 provides network functionality for medical devices within the hospital. The medical devices networked to the Medical Device server 124 can provide ongoing or continuous monitoring of the medical parameters and condition of patients overtime. Examples of such medical parameters include vital signs like pulse, body temperature, respiratory rate, blood pressure, blood content levels, etc.

The building management server 126 maintains and updates status and activity information about the healthcare facility, including for example, scheduling maintenance or regulating access to restricted locations. The mass notification server 128 may provide network functionality for facility-wide communications and broadcasts.

The computing and communication equipment located in the hospital units 102*a*, 102*b*, 102*c* may be communicatively connected by a hospital wide data communication network, referred to as the hospital communication network 130, that transfers information in the form of data signals. For example, router 104 and router 116 may be communicatively connected to the hospital communication network 130 to facilitate routing and directing communications data signals over the hospital network system 100. The hospital communication network 130 may be embodied by as a physical data communication bus with transmission hardware including conductive cables such as twisted pairs or fiber optics for transmission of electrical or optical signals. The hospital communication network 130, or portions of it, may also be configured as a wireless network to operate wirelessly such as through WiFi or IEEE 802.11 protocols. Moreover, hospital communication network 130 can be partitioned in different segments and sub-segments that are hierarchically interconnected with devices and resources in differing arrangements and gradations.

Figure 2:
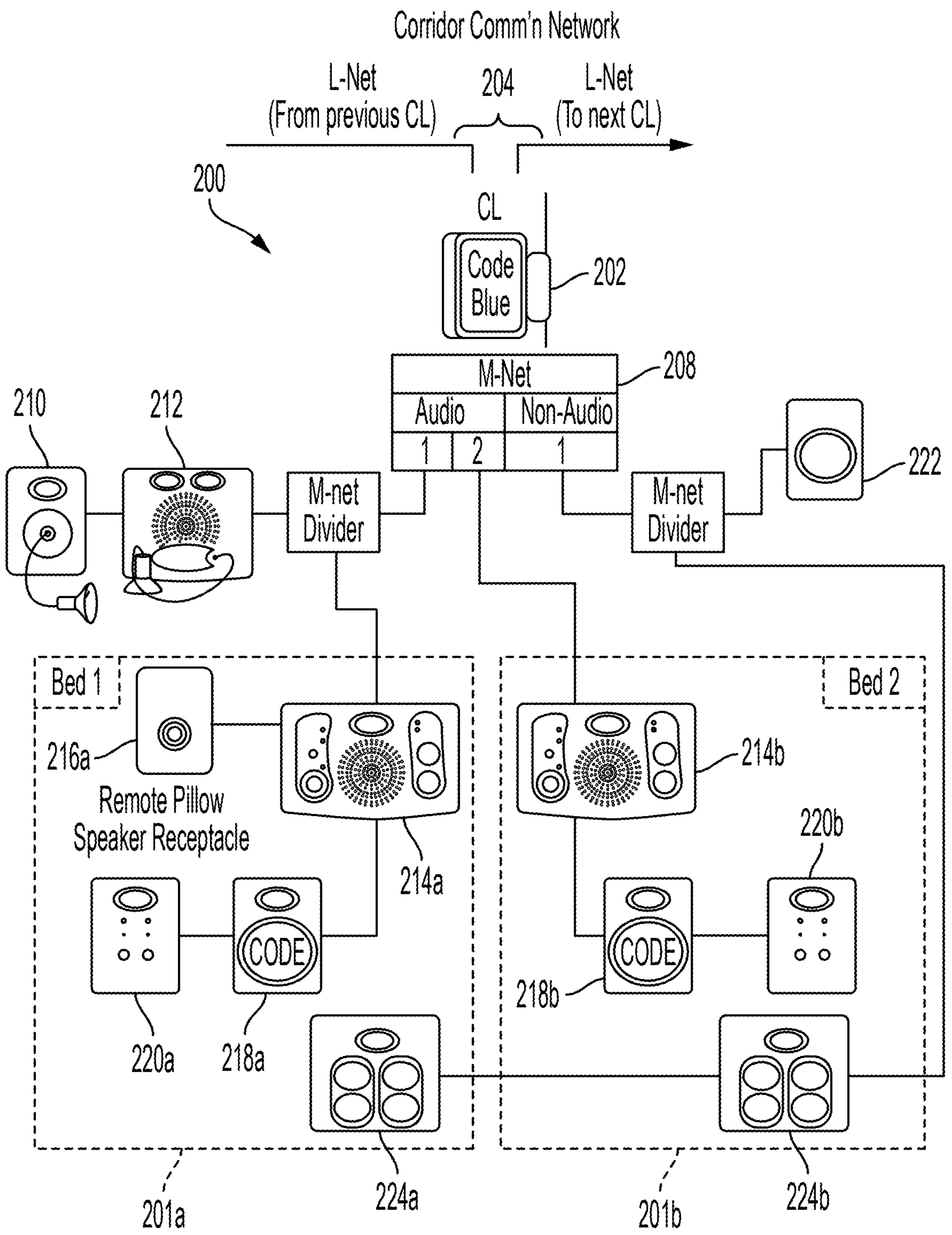
FIG. 2 illustrates patient locations or rooms operatively associated with a corridor display unit and with devices and resources in a hospital or healthcare environment.

FIG. 2 illustrates a patient location 200, which may be embodied as a patient room 200, including first and second beds 201*a* and 201*b* and a caregiver call system 206 including different call devices. As described above, the patient room can be an enclosed space within the hospital that is bounded by walls where a patient is located. In other embodiments, instead of distinct patient rooms, the patient location 200 may be partitioned by curtains or the like. The patient location 200 can be associated with a corridor display unit 202, designed in accordance with the disclosure, which provides visual information about the patient and/or room status. The visual corridor display unit 202 is typically mounted on the surface of a hallway or corridor outside of and connected with the patient room 200 and can include a lighting system that visibly lights up the corridor to annunciate the status or information about the patient inside the patient location 200. The corridor display unit may also be located at an intersection of multiple corridors to present information from a highly visible location. The corridor display unit 202 may be communicatively connected to the caregiver call system 206 by a network connector 208 and may visually respond upon activation via the call devices associated with the caregiver call system 206 to alert caregivers who may be located in the corridor or hallway as to the patient status.

In an embodiment, the corridor display unit 202 may also be communicatively connected to a corridor communication network 204 via a network connection. The corridor communication network 204 can be a segment of the enterprise wide, hospital communication network 130 described with respect to FIG. 1. The corridor communication network 204 can be a multi-drop network conduit that connectively links the visual corridor display unit 202 with other corridor display units located in the corridor or hallway and that may be associated with other patient locations 200; although other communication network topologies may be used to establish communication with the corridor display networks. Each of the corridor display units 202 may function as a network node interconnected by the common corridor communication network 204. The corridor communication network 204 can be a wired system embodied by electrical conductors such as twisted pairs for the transmission of power and data signals, referred to as Power over Ethernet (POE) connectivity; although in some embodiments, the corridor display units 202 may be configured with wireless connections to send and receive information wirelessly such as by radio frequency transmission.

The corridor communication network 204 can be communicatively connected to the caregiver call system 206 through the corridor display unit 202. In other embodiments, however, the hospital network system 100 and the caregiver call system 206 may be directly interconnected and bypass the corridor display unit 202. With respect to PoE connectivity, the corridor communication network 204 may be communicatively and operatively separated from the hospital communication network 130 via network segmentation techniques so that the corridor communication bus 204 may be dedicated for conducting the rated electrical power and current load required by the plurality of visual corridor display units 202.

The caregiver call system 206 within a patient location 200 may be interconnected with the corridor display unit 202 associated with the respective patient location through a patient location network connector 208 operatively disposed between the systems and that can be configured for audio and non-audio transmission. In the audio component, the electrical transmissions conducted through the patient location network connector 208 may be electrical signals representing audible sounds converted through microphones and speakers that serve as call device components of the caregiver call system 206. The non-audio component of the patient location network connector 208 may transmit data and power to non-audio call devices of the caregiver call system 206.

For example, audio port 1 of the patient location network connector 208 connects room pull cord stations 210 and 212 to the corridor communication bus 204 through the corridor display unit 202. Audio port 1 further connects with a pillow speaker 214*a* and its remote pillow speaker receptacle 216*a* for bed 201*a*. Audio port 1 further connects the corridor communication network 204 with a Code Blue pushbutton Station 218*a* and a dual ¼ inch jack station 220*a* of bed 201*a*. The Code Blue pushbutton Station 218*a* allows a Code Blue event to be triggered with respect to bed 201*a*, and the dual ¼ inch jack station 220*a* allows for various auxiliary call placement devices to connect and place a call.

Audio port 2 connects the corridor communication network 204 with similar call devices but for bed 201*b*. In the illustrated embodiment, these call devices include a pillow speaker 214*b* that in turn connects to a Code Blue pushbutton Station 218*b* and a dual ¼ inch jack station 220*b*. The pillow speaker 214*b*, Code Blue pushbutton Station 218*b*, and dual ¼ inch jack station 220 operate similar to their corresponding structure from bed 201*a*. Specifically, the Code Blue pushbutton Station 218*b* allows a Code Blue event to be triggered with respect to bed 201*b*, and the dual ¼ inch jack station 220*b* allows for various auxiliary call placement devices to connect and place a call.

Further, non-audio port 1 connects the corridor communication network 204 with bedside push button stations 224*a* and 224*b* for beds 201*a* and 201*b*, respectively. Additionally, non-audio port 1 connects the corridor display unit 202 to a room emergency button 222. Signaling for all of the aforementioned call devices with respect to the patient location 200 may be routed through the corridor display unit 202 and the corridor communication network 204 to the nurse call and caregiver assignment server (not shown) for processing by the hospital network system 100.

Figure 3:
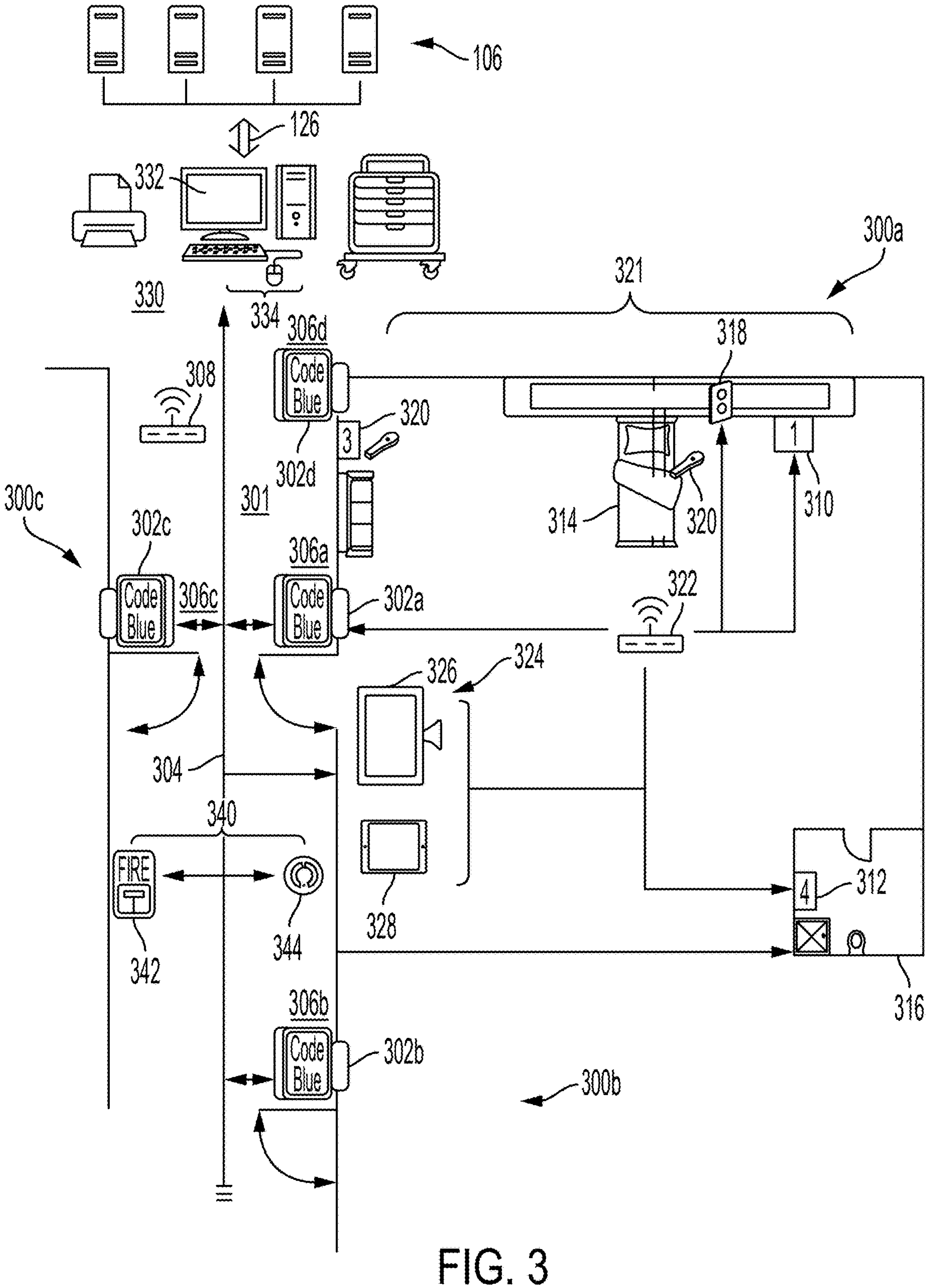
FIG. 3 illustrates an exemplary arrangement of a patient location such as a patient room including various devices and resources operatively associated with the corridor display unit.

FIG. 3 illustrates the spatial layout and possible contents of a patient room 300*a* in a hospital or healthcare facility. The patient room 300*a* is connected to the hallway or corridor 301 that may lead to other patient rooms 300*b*, 300*c* aligned along either side of the corridor 301 to provide passage there between. Mounted to a surface of the corridor 301, such as a wall or ceiling, can be a plurality of corridor display units 302*a*, 302*b*, 302*c* for annunciating visible information to caregivers in accordance with the disclosure. Each visual corridor display unit 302*a*, 302*b*, 302*c* is associated with a respective one of the patient rooms 300*a*, 300*b*, 300*c* and is mounted in the corridor 301 in close proximity to the respective patient rooms. A visual corridor display unit 302*d* can also be located within the corridor 301 at locations away from the patient rooms 300*a*, 300*b*, 300*c*, for example, at an intersection of a plurality of corridors. The corridor display units 302*a*-302*d* are mounted to or hung from a surface to increase the field of view perceptible to caregivers at the hospital or healthcare facility.

To communicatively interconnect and network the plurality of visual corridor display units 302*a*, 302*b*, 302*c*, a corridor communication network 304 can be operatively associated with the devices in the corridor 301. As described in FIG. 2, the corridor communication network 304 may be embodied as a data and/or audio bus for the transmission of information in the form of electrical signals through hardwired conductors that physically extend the length of the corridor 301. Each of the plurality of corridor display units 302*a*-302*c* is communicatively connected to the conductors of the data bus and function as a network node or hub. The data bus may also provide PoE connectivity to supply electrical power to the plurality of corridor display units To locate and distinguish among the plurality of visual corridor displays units 302*a*-302*d*, each corridor display unit may be assigned an individual and unique network address 306*a*, 306*b*, 306*c*, 306*d*. Because of the individual and unique association between specific corridor display units 302*a*-302*c* and the respective patient rooms 300*a*-300*c*, the network addresses 304*a*-304*c* can function to identify individual patient rooms within the corridor 301. The unique network address of the visual corridor display unit 302*d* may be indicative of another location in the hospital or healthcare facility such as, for example, an equipment room or stairwell. The network addresses 306*a*-306*d* of the corridor display units 302*a*-302*d* can be assigned using a unique data code or may be physically set using switches or dials on the corridor display units.

The corridor communication network 304 can also be embodied as a wireless network in which information is transmitted by radio frequency communication between the plurality of visual corridor display units 302*a*-302*d*. Wireless communication can utilize any appropriate wireless protocol such as Wi-Fi or IEEE 802.11. Each visual corridor display unit 302*a*-302*d* can maintain a unique network address 306*a*-306*d* to differentiate and distinguish themselves within the wireless network. In the wireless embodiment, the corridor communication network 304 can include a central corridor router 308 that functions as a communication hub to direct wireless data traffic among the plurality of corridor display units 302*a*-302*d*. In other embodiments, the corridor communication network 304 may be configured as a wireless chain network with wireless data exchanged directly between the corridor display units 302*a*-302*d*.

Inside the patient room 300*a* there may be located one or more pull cord stations 310 and 312, for example, arranged next to a patient bed 314 or in a bathroom 316 of the patient room 300. The pull cord stations 310, 312 are emergency alert devices that include a knob connected to a cord or string that may be pulled to activate an alarm that may be visual, audio, or otherwise. Patient room 300 further includes a pushbutton station 318 and pillow speaker 320 associated with the patient bed 314. The pushbutton station 318 is another communication device that includes one or more pushbuttons that may be depressed to signal a specific request from the patient or an attending caregiver. The pillow speaker 320 can include a microphone/speaker transducer for the conversion and transmission of audible sounds into electrical signals. The pull cord stations 310, 312, the button station 318, and the pillow speaker 320 can collectively be referred to as nurse call devices and may comprise a nurse or caregiver call system 321 to communicate messages with caregivers outside of the patient room 300*a*.

The pull cord stations 310 and 312, the button station 318, and the pillow speaker 320 are networked together to the respective corridor display unit 302*a*-302*c* and thus to the corridor communication network 304. In an embodiment, the pull cord stations 310 and 312, the pushbutton station 318, and the pillow speaker 320 may be communicatively interconnected and networked through a common patient location network connector 322. The patient location network connector 322 can be configured as wireless router that establishes a virtual wireless network through a wireless protocol like WiFi or IEEE 802.11. The common patient location network connector 322 may also be a wired system designed to establish physical hardwired connections between the pull cord stations 310 and 312, the pushbutton station 318, and the pillow speaker 320. Electrical conductors adapted for PoE connectivity to distribute electrical power and data signals may physically extend between the patient location network connector 322 and the patient room devices.

Located in the patient room 300*a* can be data input terminals 324 to record and document medical examinations and patient encounters. The data input terminals 324 can include touchscreen monitors 326 that may be mounted to the walls of the patient room 300*a* or mobile tablet computers 328 that can be carried by the caregivers during their rounds. To interface with the caregivers, the patient room data input terminals 324 can also be associated with peripheral input devices such as keyboards, mice, and touchscreen displays. The data input terminals 324 can be communicatively connected to the patient location network connector 322 by wireless or hardwired connections. The data input terminals 324 can therefore exchange data and information with the corridor communication network 304. Each of the patient rooms 300*a*-300*c* in the hospital or healthcare facility can be identically provided with data input terminals and communication devices that are also commonly connected to the corridor communication network 304.

In an embodiment, the hospital or healthcare facility may include a caregiver station 330, also referred to as a nurses' station, which may be located at the end of the corridor 301 where it is situated for convenient access to the plurality of patient rooms 300*a*-300*c*. The caregiver station 330 can function as a location for carrying out administrative tasks, medical and examination preparation, and the temporary storage of medicines and medical devices. Because the corridors 301 interconnecting the patient rooms 300*a*-300*c* may extend to and terminate at the caregiver station 330, corridor visual display units 302*a*-302*d* can be visible from the caregiver station 330.

Located at the caregiver station 300 can be one more data input terminals 332 for the entry of patient health status information collected during a patient examination. The caregiver station data input terminals 332 can be personal computers or computer devices or may be dedicated terminals, and are operatively connected with peripheral data input devices 334 such as keyboards and/or mice to interface with the caregivers. The corridor communication network 304 can extend to and be communicatively networked with the data input terminals 332 located at the caregiver station 330. The data input terminals 332 are therefore communicatively interconnected with the plurality of corridor display units 302*a*-302*c* and the communication devices located in the plurality of patient rooms 300*a*-300*c*.

The data input terminals 332 at the caregiver station 330 can also be communicatively connected to and operatively associated with the plurality of hospital network servers 106 described with respect to FIG. 1 via the hospital communication network 130. The data input terminals 332 at the caregiver station 330 therefore function as a network bridge between the corridor communication network 304 and the enterprise wide hospital communication network 130.

The data input terminals 332 at the caregiver station 330, in cooperation with the hospital network servers 106, can include functionality to run and execute medical software programs and applications within medical and healthcare context. For example, the data input terminals 332 and/or the hospital network servers 106 can store, maintain, and provide access to patient electronic medical records and other medical and clinical information. Patient electronic medical records (EMRs) refers to the organized data storage of patient specific-medical histories, conditions, and possibly clinical records. The data input terminals 332 can be used by caregivers to write data to and read data from the patient EMRs, including data reflective of patient health status, that are maintained by the hospital network servers 106.

In an embodiment, the hospital or healthcare facility can be associated with a facility alert system 340 designed to alert patients, caregivers, and other occupants to an emergency. The facility alert system 340 can include individual devices like pull stations 342 and/or detectors 344 that can be activated in an emergency to communicate an alert about the emergency such as a fire or severe weather. The pull stations 342 and detectors 344 can be located in the corridor 301 and can be communicatively networked to the corridor communication network 304. The facility alert system 340 can therefore send alerts through the plurality of corridor display units 302*a*, 302*b*, 302*c* to inform the facility occupants of the emergency.

Figure 4B:
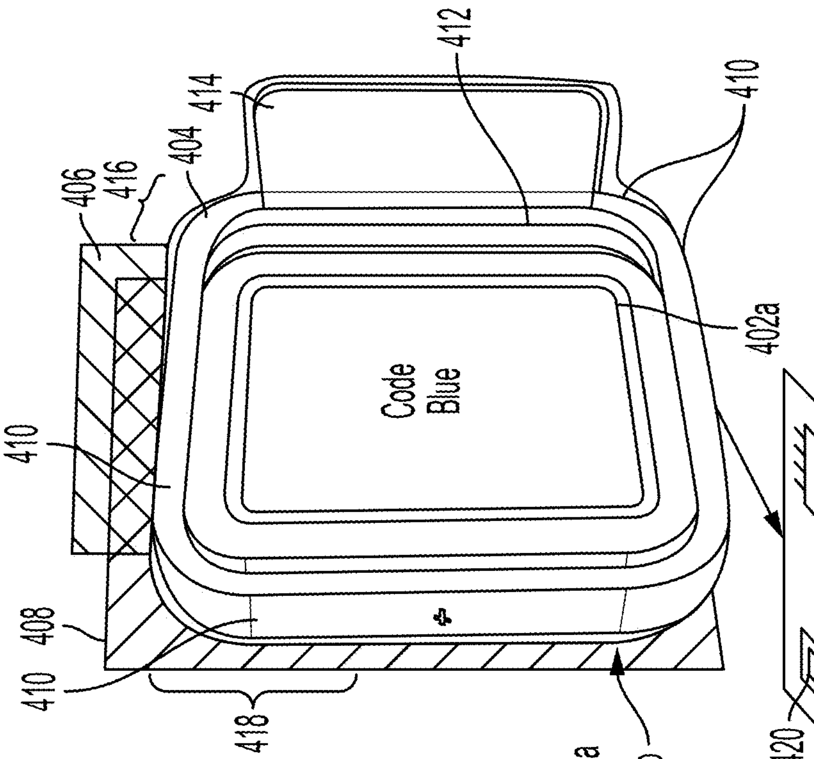
FIGS. 4*a*-4*c* are perspective views of an embodiment of the corridor display unit configured to display a plurality of different images to annunciate information to caregivers at the hospital or healthcare facility.
Figure 4C:
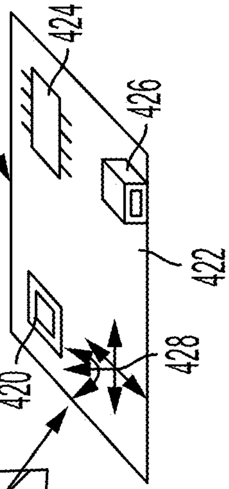
Figure 4A:
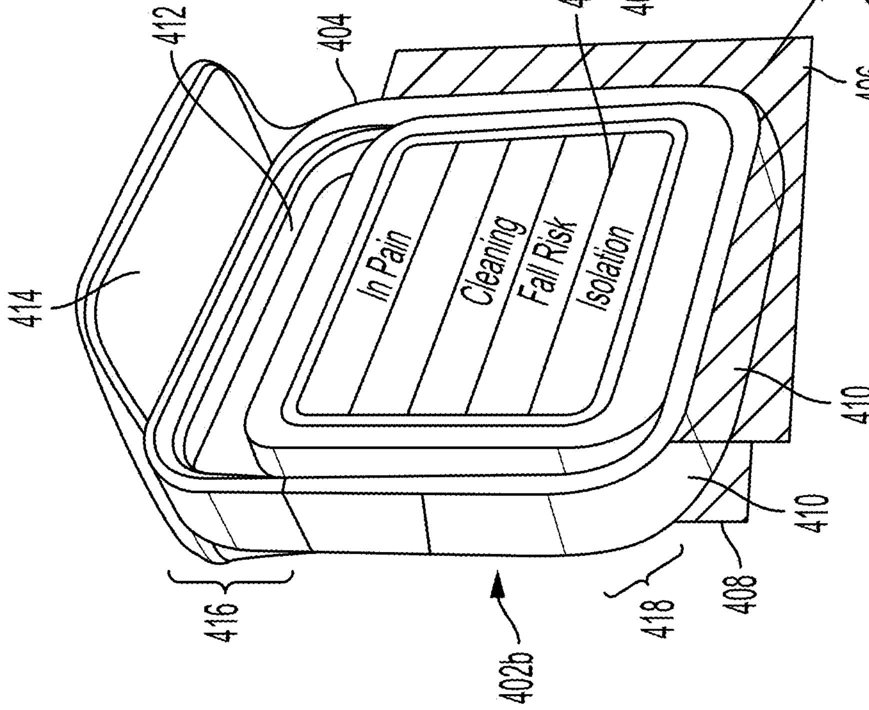

Referring to FIG. 4, there is illustrated a possible embodiment of a corridor display unit 400 in accordance with the disclosure to visibly annunciate information to caregivers within the corridor or hallway of the hospital or healthcare facility. The corridor display unit 400 can include one or more flat panel displays 402 or screens that are mounted within a frame 404. The flat panel displays 402 can be embodied as liquid crystal display (LCD) screens or light emitting diodes (LED) screens that can render visual display images, text, graphics etc. The flat panel displays 402 can include the circuitry and functionality to convert electrical data signals into rendered visual images indicative of the health status information regarding a patient or similar information pertaining to the operations of the hospital or healthcare facility. In an embodiment, the corridor display units 400 can include first flat panel display 402*a* oriented on and visible from a first visual plane 406 of the corridor display unit and an oppositely located second flat panel display 402*b* oriented on and visible from second visual plane 408 of the corridor display unit that is parallel with the first visual plane 406. The annunciation images displayed by the flat panel displays 402*a*, 402*b* are therefore visible from opposing sides of the corridor display unit 400.

The mounting frame 404 can be generally rectangular and may include four orthogonally arranged and interconnected straight frame legs 410. The interconnected straight frame legs 410 outline and enclose the first and second flat panel displays 402*a*, 402*b* and thereby define an opening or frame window 412 through which the visible display image is transmitted.

In an embodiment, to mount the corridor visual display unit 400 to a surface of the corridor or hallway, such as a wall or ceiling, the mounting frame 402 can include a mounting bracket 414 integrally attached along one of the four straight frame legs 410. The mounting bracket 414 can be generally rectangular and flat for placement adjacently against the corridor surface to support and distribute the weight and moment of the visual display unit with respect to the corridor surface. The mounting bracket 414 can be arranged orthogonal to the visual planes 406, 408. The orthogonal orientation of the mounting bracket 414 to the mounting frame 404 situates the corridor display unit 400 in the corridor so the visual planes 406, 408 project perpendicularly from the corridor surface into the corridor for ease of visibility. In an embodiment, the mounting frame 404 can situate the flat panel displays 402*a*, 402*b* so the visual planes 406, 408 are angled downward or inclined with respect to the corridor surface for improved visibility by a staff passing by. Mounting of the corridor display unit 400 to the corridor surface can be accomplished using fasteners inserted through the mounting bracket 414.

In an embodiment, to facilitate enclosure and orientation of the flat panel displays 402*a*, 402*b*, the mounting frame 404 can be a split frame in which a portion of the straight frame legs 410 are split and can be separated from each other. Accordingly, a detachable first frame part 416 can be separated from a second frame part 418, which may be associated with the mounting bracket 414, to enable insertion of the flat panel displays 402*a*, 402*b* during assembly. When the first and second frame parts 416, 418 are joined together, the mounting frame 404 constrains and fixes the flat panel displays 402*a*, 402*b* in a desired location and orientation in the corridor or hallway.

In an embodiment, to provide standalone functionality, the corridor display unit 400 can include one or more processors 420 that can be electrically mounted to a controller board 422 or printed circuit board. The processor 420 can be embodied as a central processing unit (CPU), an application specific integrated circuit (ASIC), or a field programmable gate array (FPGA) comprising a plurality of transistors and similar circuits that are capable of reading, manipulating and outputting data in electronic form. To store the program code for operation of the flat panel displays 402*a*, 402*b*, the corridor display unit 400 can include at least one non-transient programmable memory 424. The memory 424 can be random access memory or more permanent non-volatile forms of memory. The memory 424 is capable of storing the programming instructions and the data that can be read and processed by the processor 420. To interface and communicate with the corridor communication network and the electronic devices communicatively connected thereto, the corridor display unit 400 can include one or more input/output ports 426 mounted to the controller board 422 and accessible through, for example, the mounting bracket 414. The one or more input/output ports 426 can be embodied as registered jacks that form physical, releasable connections through a plurality of conductive pins or terminals. In other embodiments, the input/output ports 426 can be wireless interface connectors to communicatively connect with a wireless network through radio frequency signals. The wireless interface connector functions as a transceiver transmitting and receiving wireless data signals. To properly orientate the visual displayed images projected from the flat display screens 402*a*, 402*b* for perception by caregivers, an accelerometer or inertial measurement unit 428 sensitive to motion or magnetic orientation can be included on the controller board 422. The inertial measurement unit 428 allows the corridor display unit 400 to be mounted in multiple orientations to the wall and/or ceiling of the corridor.

FIG. 5 is schematic illustration of an arrangement for generating or rendering annunciation images from various information sources that can be displayed on the corridor display units. The arrangement may include a display controller 500 that is an electronic digital processing device or computing device designed and programmed with functionality to generate the annunciation images 504 from multiple data sources for visual display on the corridor display units 502. The display controller 500 can be physically associated with hardware components like a processor, memory, and input/out ports for data communication. The display controller 500 can be part of or reside in the corridor display unit 502 and may share the computing components described in FIG. 4*c*. The display controller 500 also can be physically separated from and in remote communication with the corridor display unit. Furthermore, the components and functionality of the display controller 500 may be distributed among the systems and subsystems illustrated in FIG. 5 or may reside elsewhere in the hospital network.

To generate an informative and contextual annunciation image, the display controller 500 can receive information from different sources that are indicative of or reflect the health condition of the patients and/or the activities and on-goings of the hospital or healthcare facility. The display controller 500 can process and organize the data and facts received to provide context for the annunciation image that is conveyed to the caregivers. This may involve manipulating, converting, and/or transforming the raw data and facts into different information or conclusions, grouping or rearranging the data and facts to provide collective or situational information, and adding or supplementing the data and facts for improved compressibility and increased understanding.

To receive data for the generation of the annunciation images, the display controller 500 can be communicatively networked with the resources and systems described herein. For example, the display controller 500 can be communicatively interconnected with the plurality of hospital network servers 106 described with respect to FIG. 1. The network servers 106 include further sub-servers such as an Electronic Medical Records/Admission/Discharge/Transfer (EMR/ADT) server 118, a Real Time Location System (RTLS) server 120, an Assignment Scheduler server 122, a Medical Device server 124, a building management server 126, and a mass notification server 128. The hospital communication network 130 establishes telecommunications connectivity between the network servers 106 and display controller 500.

The display controller 500 can also be communicatively interconnected with the caregiver call system 321 including the caregiver call devices like pull cord stations 310, 312, pushbutton stations 318, and speakers 320. For priority and immediacy, the caregiver call system 321 may directly communicate with the display controller 500, for example, through the patient location network connector 322. In other embodiments, communications from the caregiver call system 321 may be routed through the other communication networks described herein.

To receive updated patient or facility information, the display controller 500 can also be communicatively interconnected with the data input terminals, including the patient room data input terminals 324 and the caregiver station data input terminals 334. The display controller 500 and data input terminals 324, 324 can exchange data and information through the hospital communication network 130, the corridor communication network 304, or both. Further, the display controller 500 can be communicatively interconnected with the facility alarm system 340, for example, in association with the building management server 126 and/or mass notification server 128. To establish priority in an emergency, the facility alarm system 340 can be directly connected with display controller 500 through the corridor communication network 304.

The contextual annunciation images 504 generated by the display controller 500 can include data and convey information of different types and related to different subjects. By way of example, FIG. 5 schematically illustrates Table 510 of the types of data and information that can be used to generate the annunciation image, and are therefore represented by the annunciation images. Table 510 is presented for non-limiting explanatory purposes, and the data and information therein may be altered, varied, supplemented or may be assigned, defined, or categorized in different ways.

For example, the data and information may be prerecorded data and information 512 in that it existed prior to generation of the annunciation image 504. Prerecorded data and information 512 may be static and can be obtained by a prior examination or from a predetermined schedule. Prerecorded data and information 512 can reside in memory or data storage associated with the display controller 500 and can be retrieved by the display controller when generating the annunciation image 504.

The data and information may be real-time 514, meaning the display controller 500 obtained it contemporaneously with the generation of the annunciation image 504. Real-time data and information 514 can originate from ongoing monitoring or be obtained during an activity or an event. Real-time data and information 514, as presented in the annunciation image 504, may be responsive and may be reflective of a current change in patient condition or the hospital activities. The real-time data and information 514 can be updated continuously and continually communicated to the display controller 500 or the processing systems associated there with.

The data and information may originate from different sources and concern different subjects. For example, the data and information can be about or concern patient status 516, such as the patient's health status or medical condition. Furthermore, the patient status 516 can be prerecorded or real-time data or information 512, 514. An example of prerecorded patient status data 516 can be a risk assessment or presented medical condition observed or reported during a medical examination. The prerecorded patient status data 516 can be stored in and retrieved from a patient electronic medical record (EMR) associated with the Electronic Medical Records/Admission/Discharge/Transfer (EMR/ADT) server 118. An example of real-time patient status data can be a patient request made using the caregiver call system 321 or can be medical parameters continually measured by the medical devices associated with the Medical Device server 124.

The data and information for generating the annunciation images can concern or be reflective of the patient location status 520. The data and information about the patient location status 520 includes information about or originating from the patient locations like patient rooms. Patient location status data 520 can also be prerecorded or real-time. Examples of prerecorded patient location status data may include assigned occupancy data such as the named patient assigned to the patient room as provided by the EMR/ADT server 118, cleaning or maintenance schedules, medical equipment present at the patient location, etc. Examples of real-time patient location status data include present occupancy data noting the presence of attending caregivers or visitors, or monitored environmental conditions about the patient location like room temperature, humidity, lighting, etc.

The data and information may also be or regard facility status data 522 about the activities or conditions of the hospital or facility. An example of real-time facility status data 522, the display controller 500 can be directly connected with the facility alarm system 340 and can be configured to display an annunciation image upon activation of, for example, the alarm pull station 342. Directly connecting the display controller 500 and facility alarm system 340 ensures data and information concerning facility emergencies may assume priority over the corridor display units 502. Examples of prerecorded facility status data 522 can be navigational information such as assigned room numbers, corridor identifiers, stairwell indicators, etc.

The data and information can also be caregiver-faculty status data 524 about or intended for the caregivers and other faculty present in the hospital or healthcare facility. An example of prerecorded faculty status data 524 can be the identification of the caregivers, including nurses and physicians, assigned to a patient at a particular patient location. An example of real-time faculty status data 524 includes instant messaging directed to individual caregivers whose locations or whereabouts can be determined by the RTLS server 120 and communicated to the display controller 500 operatively associated with the relevant corridor display unit 502. Another example of real-time faculty status data 524 can be an assistance request sent over the hospital communication network 130, for example, from a caregiver to an orderly.

In an example, the faculty status data 524 can be adapted to specific or intended caregivers or staff based on a language preferences. For example, using the locations or whereabouts of a particular caregiver as determined by the RTLS server 120, the display controller 500 can be configured so that the faculty status data 524 directed to the appropriate corridor display unit 502 is presented in the preferred language of the intended recipient. Additionally, faculty status data may be presented in an alternatively repeating manner in different languages on the corridor display unit 502 for better communication with the healthcare facility staff and faculty.

The functionality for generating contextual annunciation images about the data and information received is provided by the subcomponents and intra-operational arrangement of the display controller 500. While the display controller 500 is illustrated as a single structure, the functionality and actions may be distributed among different devices. Furthermore, while the display controller 500 is illustrated with a single associated corridor display unit 502, the display controller 500 may be networked with a plurality of corridor display units 502 and each corridor display unit 502 can be networked with a plurality of display controllers 500.

To receive and organize the data and information from the resources described above, the display controller 500 can include a logic unit 530. The logic unit 530 is a hardware or firmware component with circuitry to perform logical operations that analyze, sort, and/or prioritize the data and information received. The logic unit 530 can be operatively associated with a logic base 532 that includes rules and definitions embodied as executable software written in programming code. The coded instructions and definitions in the logic base 532 may be periodically supplemented or updated by software upgrades. In addition to pre-programmed rules and logic definitions, the logic unit 530 can include a machine-learning algorithm or application in which the logic unit relies on or utilizes past or historic data to autonomously make decisions with respect to present circumstances.

In an example, the logic rules and definitions in the logic base 532 can include prioritization rules which prioritize the data and information received from the resources for including in the annunciation image 504. The data and information may be assigned or associated with priority or hierarchy ranks, such as the origin of the data or the categorization of the data. For example, patient status information 516 originating as real-time data 512, or data originating from a caregiver call system 321, can be assigned higher priority than prerecorded facility status data 522. The logic unit 430 can select or discard the data for inclusion in the annunciation images based on the priority ranks.

The logic unit 530 selects data and information as inputted for generation of the annunciation image 504 that is passed onto an image generation engine or image generator 534. The image generator 534 is configured for converting the selected data to numerical, textual or symbolic imagery comprehensible and understandable to the caregivers and others. The image generator 534 can be operatively associated with an image base 536 storing, as electronic data, text, graphics, visual objects, etc. from which the annunciation image can be generated. In an exemplary embodiment, the image base 536 can include readable text or characters 538, graphical images or symbols 540, colored palates or brightness settings 542, texture mappings, other visual or optical data, objects, templates, rendering settings, etc., useful for the creation of the annunciation images. The image generator 534 can be configured to resize and rearrange the plurality of images selected for inclusion in the annunciation image 504 based on, for example, the rules and definitions in the logic base 532.

The image generator 534 combines, aggregates, and/or formats the data from the logic unit 530 and the input from the image base 536 to produce the annunciation image 504 as a computer readable image file 544 that can be rendered on the corridor display unit 502. The image files 544 may be stored in a controller buffer or controller memory 546 associated with the display controller 500. The image files 544 or portions thereof can be preconstructed and available for selection, or the image generator 534 can dynamically generate image files 544 in response to data and information passed from the logic unit 530. The image files 544 can be raster images, bitmaps, or any other suitable graphics format.

The display controller 500 can include other components and functionality to enable generation of the contextual annunciation images 504. For tracking and counting time, a digital clock 548 can be included or associated with the display controller 500. The digital clock 548 enables the display controller 500 to time and sequence events and can synchronize the display controller with other networked systems. To identify the appropriate corridor display unit 500 and other components with which the display controller 500 may be networked, a readable network address list 550 can be associated with the controller. The address list 550 enables the display controller 500 to send the image files 544 to the appropriate corridor display unit 500 for rending as an annunciation image 504.

In an embodiment, the logic unit 530 can use the address list 550 to analyze and select input data and information for inclusion into the annunciation image 504. For example, specific data and information may be relevant for display at particular locations within the hospital or facility, and the physical location of the corridor display unit 502 obtained from the address list 550 can be used to select, designate, generate, and route the annunciation image 504 including the relevant information accordingly. The relevant prerecorded and/or real-time data and information 512, 514 is routed to and displayed on the appropriately located corridor display units 502. The address list 550 can be used by the display controller to select patient specific patient health status data 516 and patient location status data 520 to the display controller 504 spatially associated with the appropriate patient room. Likewise, the display controller 504 can use the address list 550 to route facility status information to display controller 504 at other places about the hospital or healthcare facility to indicate the location of medical equipment or facility equipment, or location of specific activities such as clinical diagnostics and medical or laboratory testing.

Figure 6:
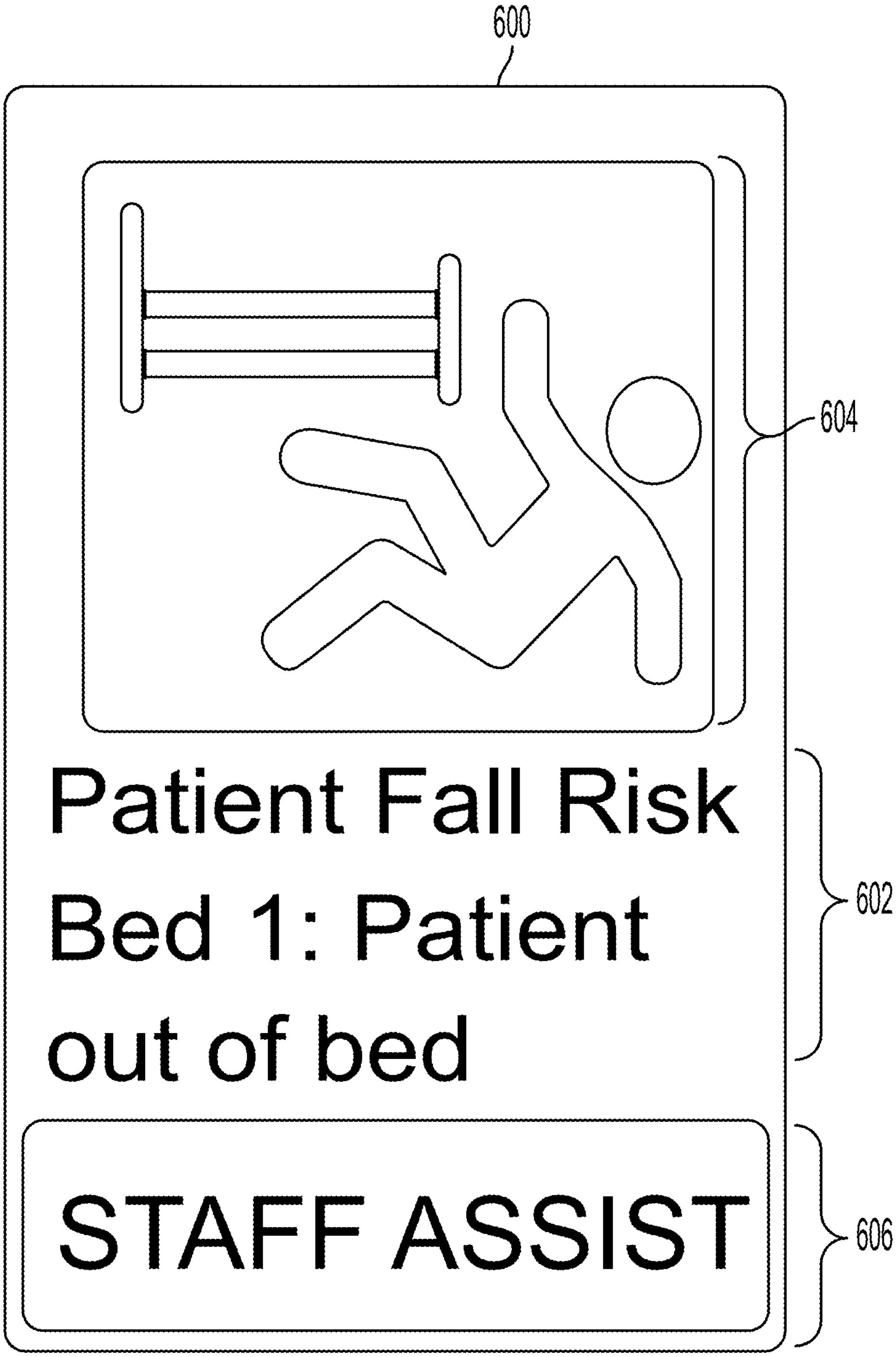
FIG. 6 is a plan view of an embodiment of an annunciation image that may be rendered on the corridor display unit and that includes real-time or prerecorded patient health status information.

Referring to FIG. 6, there is illustrated an embodiment of a contextual annunciation image 600 that can be displayed on the visual corridor display unit to convey relevant information about patient health care status, patient location status, or other activities occurring at the hospital or health facility. The annunciation image 600 can include a textual component 602, or text, and a graphical component 604 such as a static icon. The textual component 602 may convey patient status information about the patient assigned to the particular patient location 300 associated with the visual corridor display unit 302 referenced in FIG. 3. For example, the textual component 602 of the annunciation image 600 can state "Patient Fall Risk" to announce that the Patient assigned to the patient location has been assessed as a fall risk. In the example wherein the patient status is an assessment of the patient being a fall risk, that information may have been prerecorded, for example, during an earlier patient examination.

To complement and provide context for the patient status information provided by the annunciation image 600, the graphical component 604 may be a static icon, symbol, or caricature representative of the patient status information associated with the patient assigned to the patient location. For example, the graphical component 604 can be a pictorial figure or symbol representative of relevant patient health status information and may be distinct from the textual component 602. In the embodiment of the annunciation image 600, the graphical component 604 can be a stick figure composed of lines and circles representing the patient and arranged in a pose to convey that the patient has been assessed as a fall risk. The graphical component 604 may be associated with the textual component 602 of the annunciation image 600 by the display controller at the time the prerecorded patient status data is entered, and may be simultaneously displayed on the visual corridor display unit.

In addition to visually presenting prerecorded patient status information, the annunciation image 600 can also display real-time patient status information associated with the patient assigned to the patient location. In the example where the patient has been assessed as a fall risk, the real-time patient status information may be indicative of the physical condition of the patient and whether that implicates or increases the risk of falling. For example, if the patient has moved out of bed, the real-time patient status information may announce visually or audibly "Patient out of bed" and the display controller may incorporate that announcement as a textual component 602 into the annunciation image 600. In an embodiment, the prerecorded data and information can be included in the annunciation image 600 and/or announcement by default, or an idle state, and the real-time data and information can be included in response to a real-time occurrence or event, similar to an alert or an interrupt. The real-time data and information may take priority over the prerecorded data and information.

With reference to FIG. 5, the physical condition of the patient being out of bed may be determined using the RTLS server 120 through monitoring of an RTLS tag worn by the patient, a sensor associated with the patient bed, or by otherwise determining that the patient is out of bed. To draw attention to the increased risk associated with the physical condition of the patient, the display controller 500 can also integrate a staff alert message 606 that reads "STAFF ASSIST" into the annunciation image 600 directed to the relevant corridor display unit 502. To increase awareness, the staff alert message 606 may be conspicuously configured by including a textual component 602 like "STAFF ASSIST" that is highlighted in an appropriate color, and may be caused to flash or blink.

Figure 7:
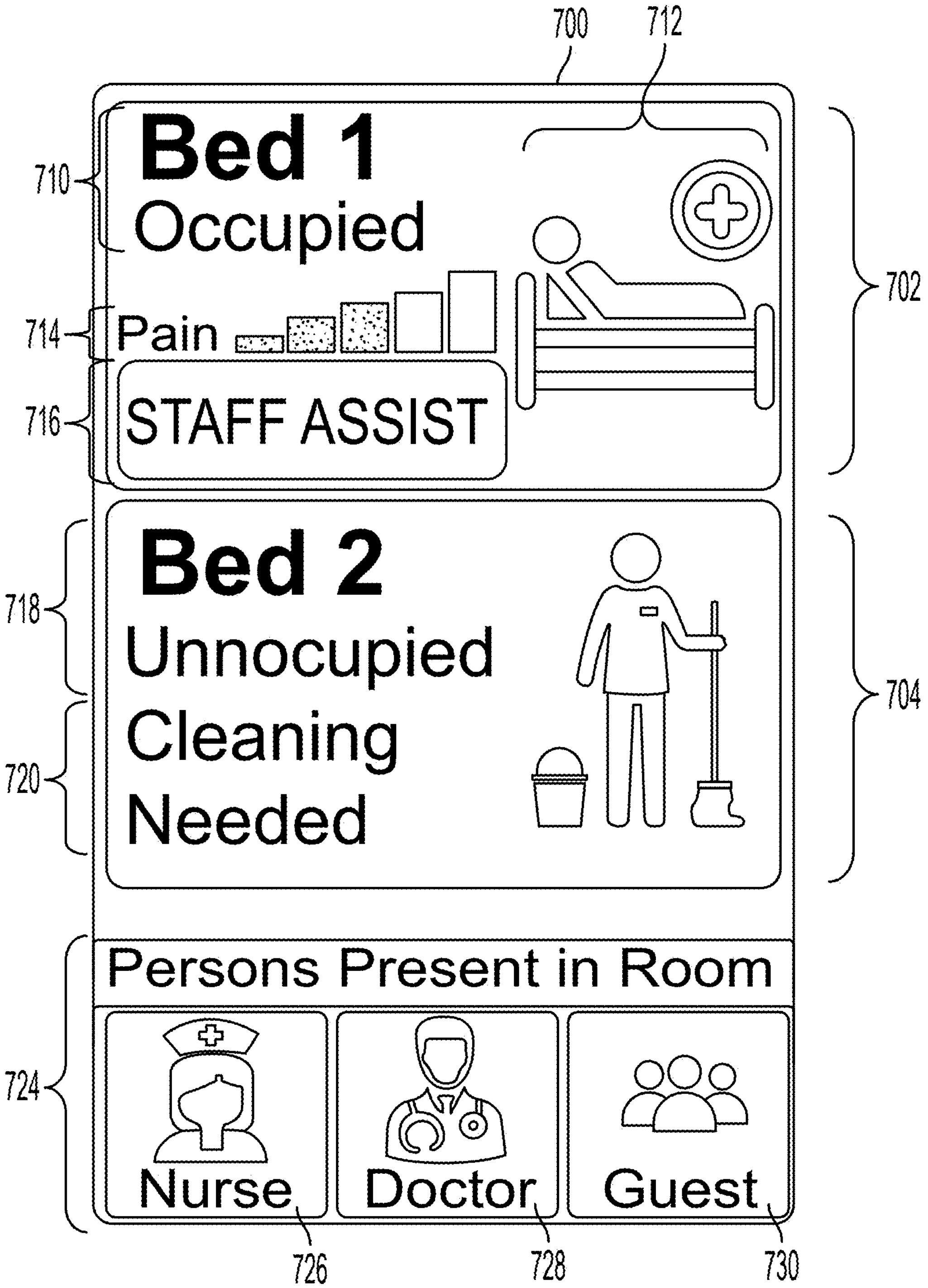
FIG. 7 is a plan view of an embodiment of a partitioned annunciation image indicative of data and information associated with two patient locations.

FIG. 7 illustrates an embodiment of a partitioned corridor annunciation image 700 that can combine and display information about two or more patient locations. For example, the partitioned annunciation image 700 can include status information about a patient in a first patient location designated as "Bed 1" and about a second patient location designed as "Bed 2." The partitioned annunciation image 700 can be partitioned into a first display area or display partition 702 and a second display area or display partition 704 to separately display the status information related to the first and second patient locations simultaneously on the same corridor visual display unit. The display controller 500 can include programming and functionality to associate the information related to the first and second patient location with the respective first and second display partitions 702, 704 and to format the first and second display partitions for presentation together as the partitioned annunciation image 700. The display controller 500 can include programming and functionality to separately and individually regenerate and update the first and second display partitions 702, 704 of the partitioned annunciation image 700 to update the patient status information or patient location information.

The first and second display partitions 702, 704 may include both textual components and graphical components. For example, the first display partition 702 can include a textual component 710 indicative that the first patient location "Bed 1" is "Occupied" to indicate that a patient has been assigned to and is present at the first patient location. To supplement the textual component, the first display partition 702 can also include a graphical component 712 such as a caricature of a patient in a bed. In FIG. 7, the first display partition 702 can also include prerecord patient status information 714 such as "Pain" level that may have been assessed during a prior medical examination and can include real-time patient status information 716 such as a "STAFF ASSIST" that may be triggered by real-time monitoring of the patient in the first patient location, for example, via the caregiver call system 321 or RTLS server 120 associated with the first patient location. The occupancy status can be augmented with other patient status information.

The second display partition 704 can be indicative of the patient location status through a textual component 718 such as the occupancy status of the second patient location, for example, that the second patient location "Bed 2" is "Unoccupied." The second display partition 704 may also represent activity information about the second patient location through a textual component 720 stating "Cleaning Needed" and a graphical component 722 such as a caricature or icon of an individual with a mop and bucket to message that the patent location requires cleaning. Other examples of patient location status information can include physical aspects of the room such as room temperature, room humidity, lighting on or off, blinds up or down, room pressure, etc. Information regarding the patient health status and the patient location status can be presented simultaneously as part of the partitioned annunciation image 700 or may be alternately and sequentially displayed on the corridor display unit.

The partitioned annunciation image 700 can also include information about the patient location status in the embodiment of present occupancy status 724. The present occupancy status 724 can be indicative of individuals whom may be physically present in the first and/or second patient locations associated with the visual corridor display on which the display controller renders the partitioned annunciation image 700. For example, the present occupancy status 724 can include textual components and graphical components representing individuals present in the patient location in the embodiment of a nurse image 726 having the title and caricature icon of a nurse, a doctor image 728 having the title and caricature icon of a doctor, and a guest image 730 having the title and caricature icon of patient guests. Referring to FIG. 5, the display controller 500 can determine occupancy of the patient location using the RTLS system 120, or caregivers and other individuals may input their presence using the data input terminal 324 at the patient location. Regarding registered staff and caregivers, the nurse image 726 and/or doctor image 728 can include names and titles, for example, as determined with the assistance of the RTLS server 120 and/or Assignment Scheduler server 122.

Figure 8:
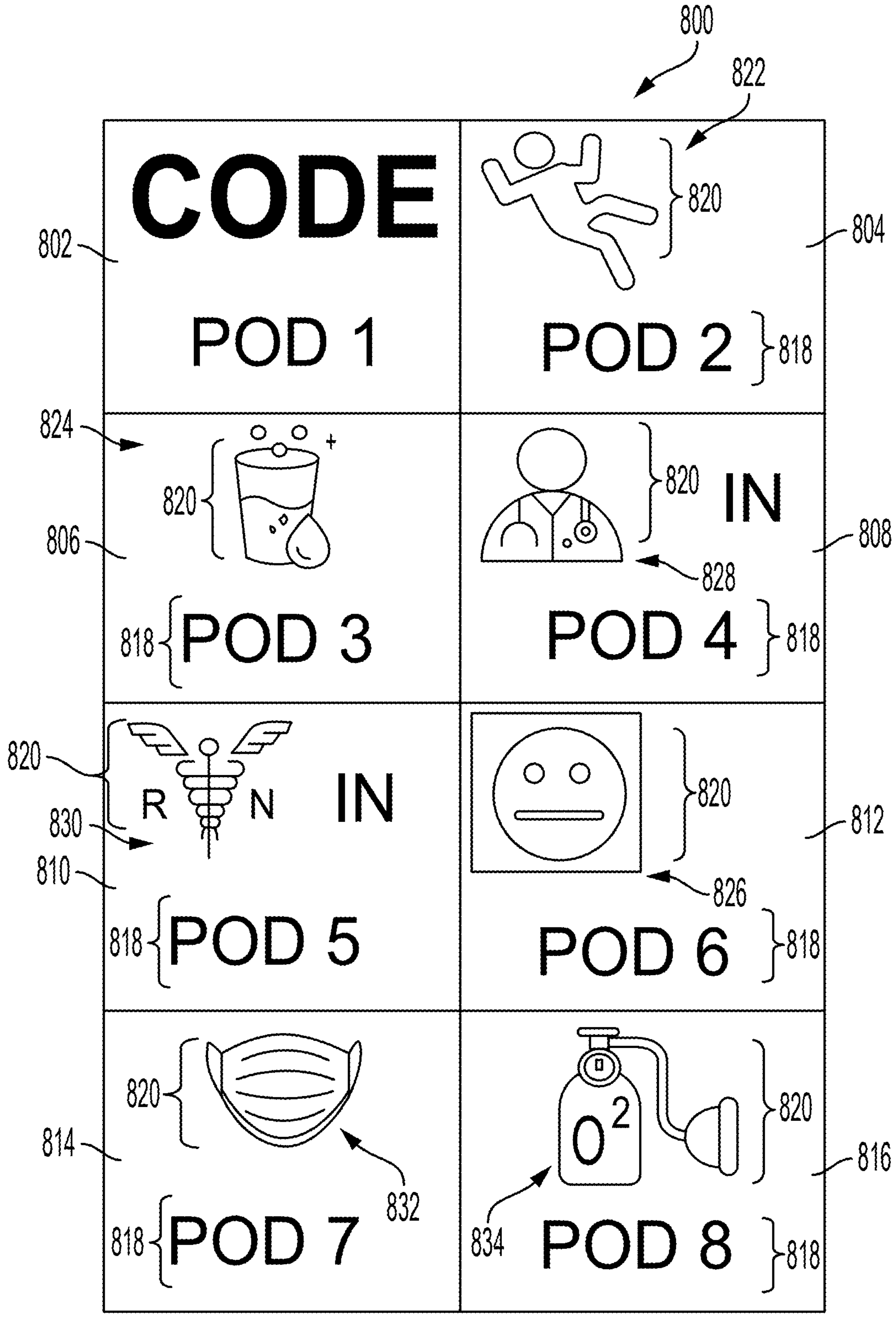
FIG. 8 is a plan view of a plurality of partitioned annunciation images that is presented in partitioned arrangement on the corridor display unit displaying data and information associated with a plurality of patient locations.

FIG. 8 illustrates another embodiment of a partitioned annunciation image 800 that is partitioned to combine information associated with a plurality of different patient locations. As described above, in some hospitals and healthcare facilities, the patient locations may be separated and cordoned by curtains or dividers such that multiple patient locations are spatially associated within the same larger room. The partitioned annunciation image 800 may therefore be partitioned into a first display partition 802, a second display partition 804, a third display partition 806, a fourth display partition 808, a fifth display partition 810, a sixth display partition 812, a seventh display partition 814, and an eighth display partition 816.

The display partitions 802-816 may include textual components 818 such as the assigned location title and graphical components 820 such as static icons or caricatures visually representing patient health status or patient location status. By way of example, the graphical components may be indicative of patient status related to a fall risk 822, a patient request 824 such as for a drink, patient disposition 826 such as a numerical or graphical pain rating, occupancy status via a doctor image 828 or nurse image 830, and information regarding activities associated with patient location status such as infectious alerts 832 or oxygen use 834. The foregoing static icons and caricatures are representative and the partitioned annunciation image 800 can include other textual components and graphical components conveying information about the patient health status or patient location status.

Figure 9:
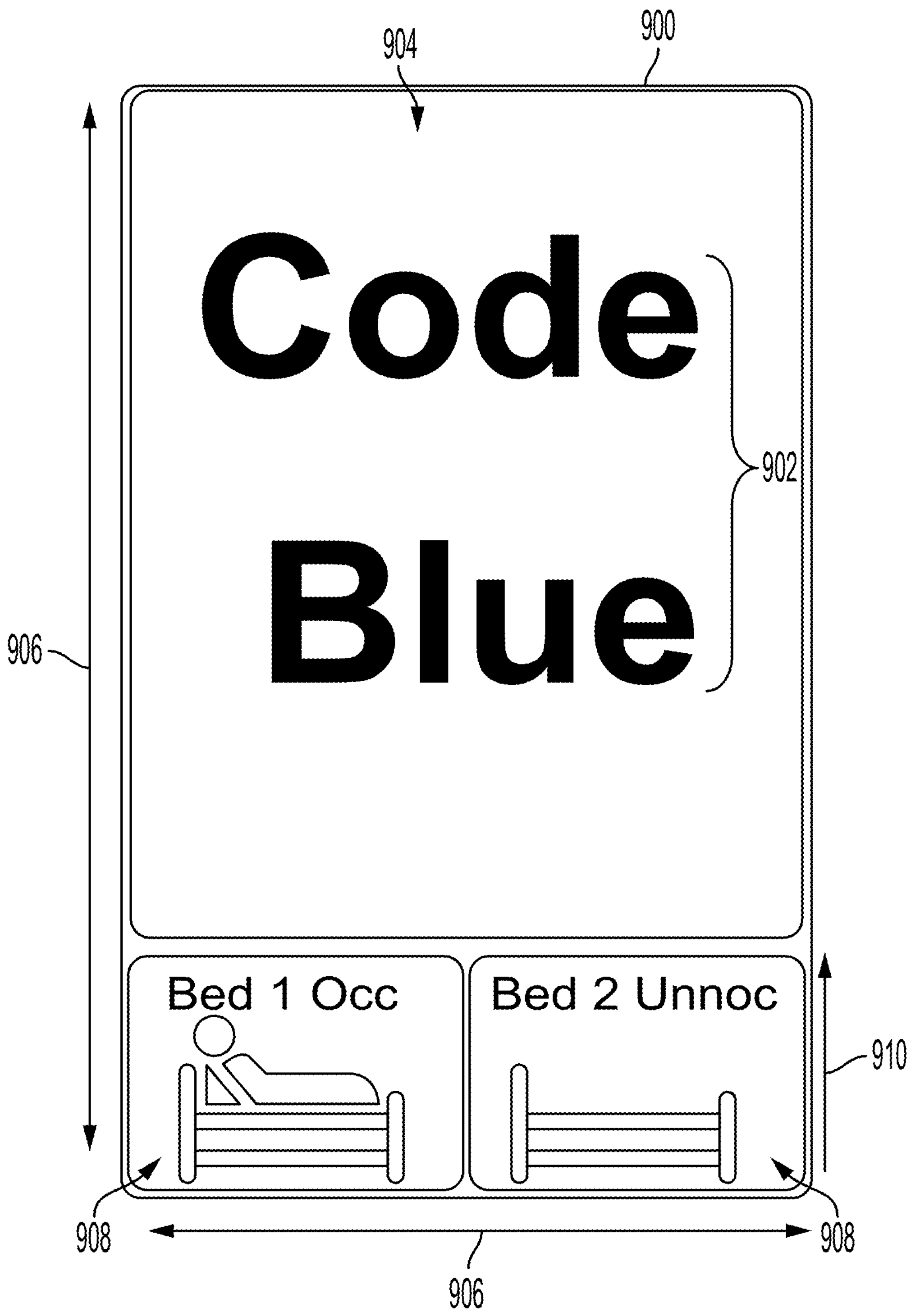
FIG. 9 is a plan view of an embodiment of an annunciation image in the embodiment of an emergency alert image that may be displayed during a code blue emergency.

FIG. 9 illustrates an annunciation image in the embodiment of an emergency alert image 900 which may be a type of real-time patient status information. For example, with reference to FIG. 5, in the medical emergency, the patient or a caregiver attending to the patient may use the pushbutton station 318 associated with the call system 321 to initiate a code blue alert. The code blue alert may be communicated from the code blue pushbutton 318 to the display controller 500 through the corridor communication network 304. The display controller 500 can generate and direct an image file 544 corresponding to the emergency alert image 900 in FIG. 9 for rendering and display on the associated corridor display unit 502.

By way of example, as illustrated in FIG. 9, the emergency alert image 900 can be made noticeably conspicuous and can include a textual component 902 overlaid on a colored background 904. To increase noticeability, the display controller 500 can format and render the size of the emergency alert image 900 to occupy and comprise a majority of the viewable display size 906 of the corridor display unit. The emergency alert image 900 may be prominently viewable from a distance. The previous annunciation image 908 previously rendered may be reduced in size with respect to the viewable display size 906 to minimize the annunciation image rendered on reduced display partition 910 to show the larger emergency alert image 900. The logic unit described in FIG. 5 can be programmed with logic rules and definitions to assess and resize the components of the annunciation images. The emergency alert image 900 may remain until the emergency has been cleared. In an embodiment, a plurality of corridor display units can operate in concert to display emergency alert images 900 in sequence to guide or direct staff to the patient location from where the emergency originated.

In an embodiment, the emergency alert image 900 can be initiated and triggered by real-time monitoring and assessment of the medical condition of the patient. For example, referring to FIG. 3, the patient in an assigned patient location may be subject to ongoing or continuous monitoring of various medical conditions and parameters via suitable medical monitoring devices. In the event the monitored medical parameters become critical, the medical monitoring device may trigger or initiate an alarm signal communicated to the Medical Device server 124 among the network servers 106. As a result, the Medical Device server 124 transmits and pushes an appropriate data signal via the hospital communication network 130 and/or the corridor communication network 304 to the designated corridor display unit 302*a*, 302*b*, 302*c* associated with the patient room 300*a*, 300*b*, 300*c* from where the medical emergency alert originated. The network addresses 306*a*, 306*b*, 306*c* assigned to the corridor display units 302*a*, 302*b*, 302*c* can be used to route the data signal to the correct corridor display unit Multipole corridor display units 302*a*, 302*b*, 302*c*, can be made to operate in concert with respect to the proximity and location of the emergency using the network addresses 306*a*, 306*b*, 306*c*.

Figure 10:
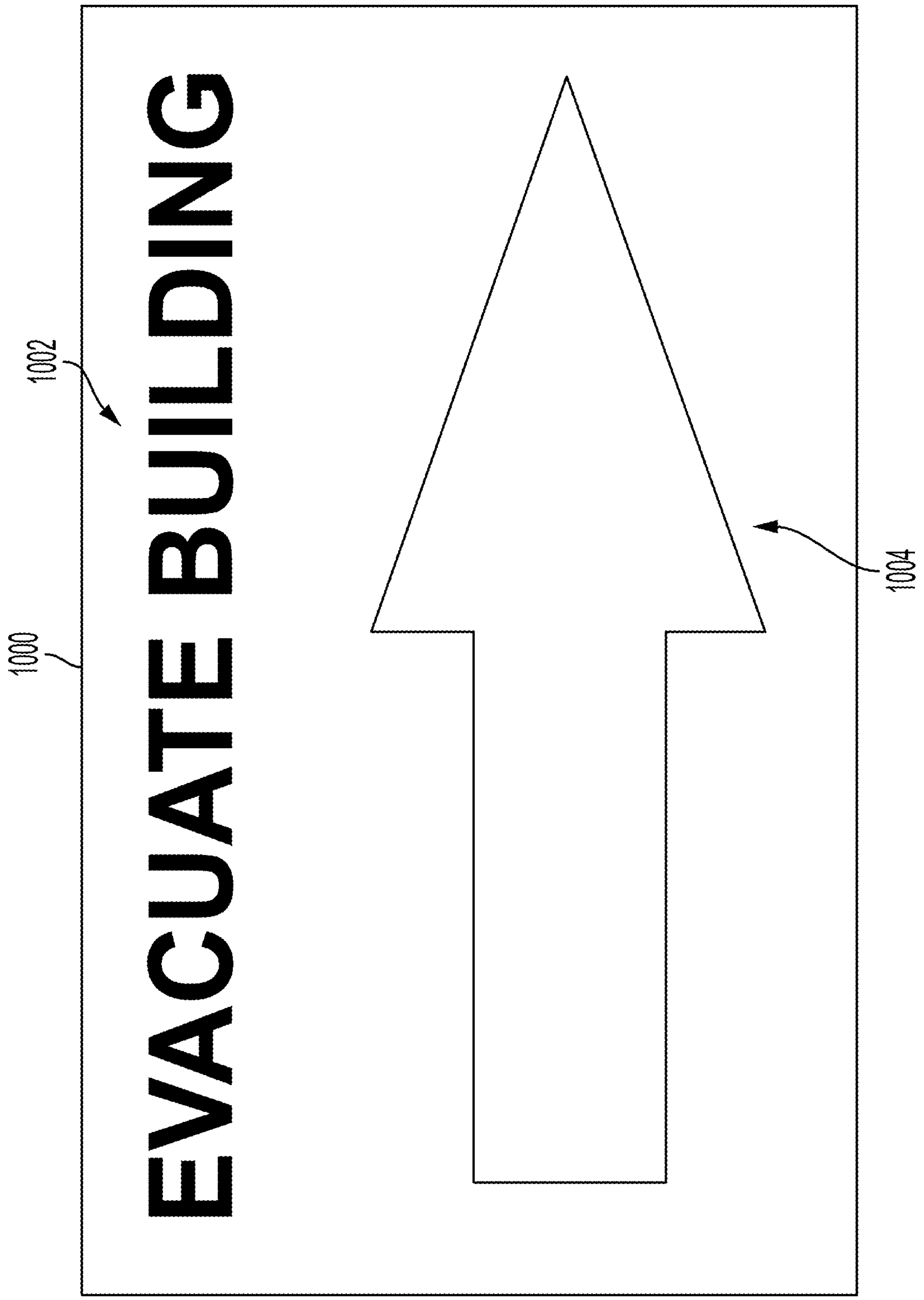
FIG. 10 is a plan view of an annunciation image in the embodiment of an emergency navigation or wayfinder image that may be displayed on the corridor display unit.

FIG. 10 illustrates an annunciation image in the embodiment of a navigation or wayfinder image 1000. For example, in the event of a facility emergency such as a fire or severe weather, which can be registered by the building management server 126 and/or the mass notification server 128, the wayfinder image 1000 can be rendered on the corridor display units to guide and assist patients, caregivers, and staff in evacuating the hospital or healthcare facility. The wayfinder image 1000 can include a textual component 1002 conspicuously announcing "EVACUATE BUILDING" and a graphical component 1004 such as an arrow indicating the appropriate exits. With reference to FIG. 5, in an embodiment, the display controller 500 can use the network address list 540 and the network addresses assigned to the individual corridor display units 502 to direct data signals to the appropriate corridor display units 502 to facilitate evacuation. The display controller 500 can be programmed to direct data signals to a group of corridor display units 502 to operate in tandem by displaying a sequential series of annunciation images to guide evacuees. In another embodiment, the wayfinder images 1000 can be configured to direct emergency personnel to locations in the hospital or healthcare facility, for example, to patient locations accommodating patients who require special assistance during emergencies or evacuation.

Figure 11:
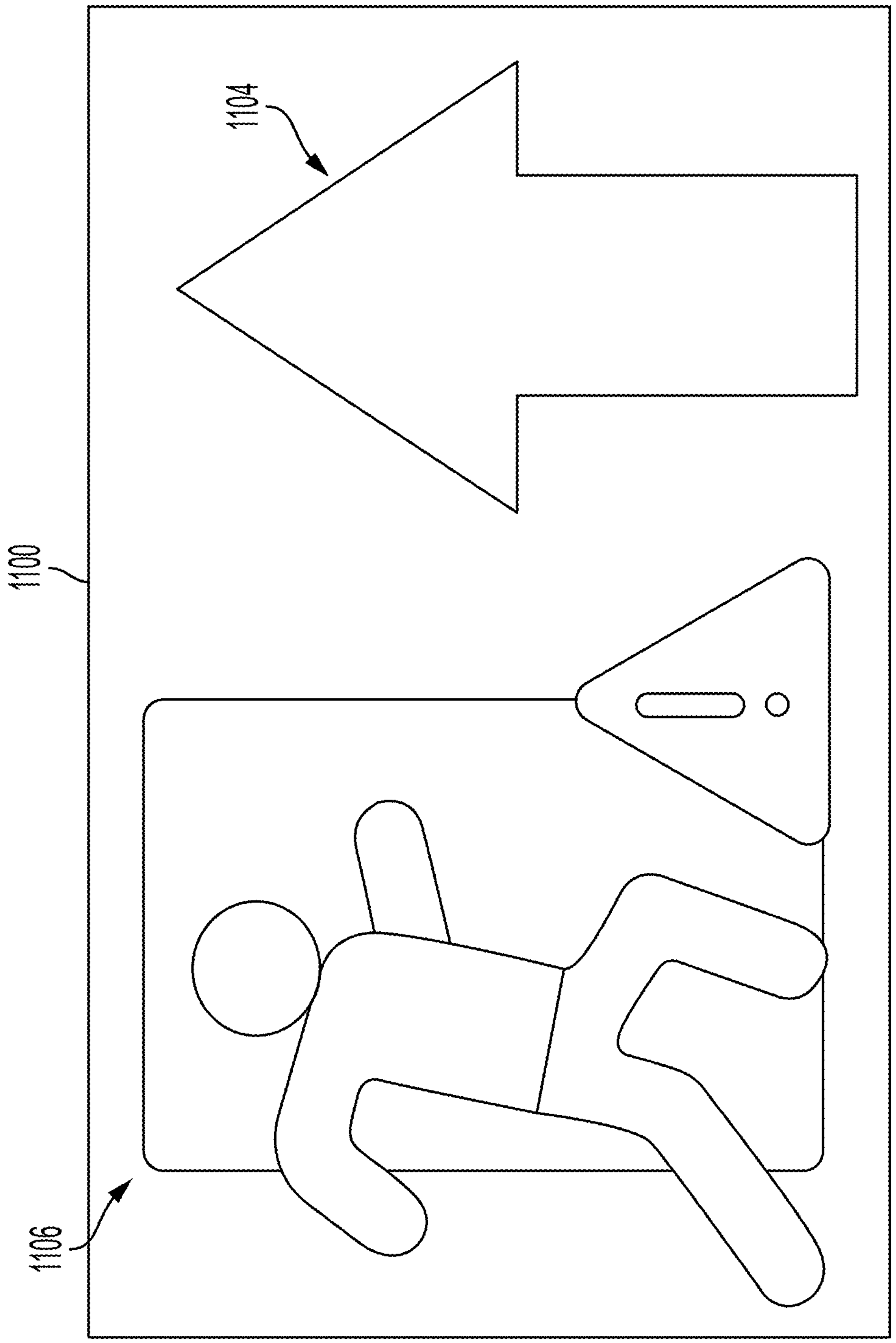
FIG. 11 is a plan view of an annunciation image embodied as another embodiment of an emergency navigation or wayfinder image.

FIG. 11 illustrates an annunciation image that may be another embodiment of a navigation or wayfinder image 1100 to convey evacuation information. The wayfinder image 1100 can be comprised of conspicuous graphical components 1104, 1106 to facilitate evacuation. In an embodiment, a plurality of corridor display units can operate in concert to sequentially display wayfinder images 1000 or 1100 in coordination to lead occupants to emergency exits at predetermined locations. The building management server 126 may utilize the network addresses associated with the plurality of corridor display units 500 and their prearranged locations in the corridors to direct the sequential display of the wayfinder images 1000, 1100 to facilitate wayfinding guidance during an emergency.

Referring to FIG. 3, the plurality of visual corridor display units can operate in cooperation with the network servers 106 to facilitate period rounding performed by caregivers and the staff. For example, the Assignment Scheduler server 122 can include a scheduler system that may be a data table assigning caregivers with particular patient locations 300*a*-300*c* and scheduling their rounds to check on the patients therein. The Assignment Scheduler server 122 can cause the plurality of visual corridor display units 302*a*-302*c* to display annunciation images to indicate to caregivers the patient locations 300*a*-300*c* according to a scheduled order. The annunciation images can be comprised of text components and/or graphic components for appropriate guidance. The Assignment Scheduler server 122 can cooperate with the RTLS server 120 to automatically track caregiver locations within the hospital or healthcare facility to direct annunciation images to the appropriate corridor display unit 300 proximate to the concerned caregiver to guide and direct them through their rounds.

In a further embodiment, the visual corridor display units can cooperate with the RTLS server 120 to direct or assist caregivers and staff in activities based on proximity. For example, the images and information projected on a particular visual corridor display unit at a fixed location may be tailored and designated for an intended recipient within the same proximity, as determined through the RTLS server 120. The projected images and information can be intended to assist the caregiver, for example, in navigating the healthcare facility or in locating equipment or medical supplies.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hospital network system comprising:

a plurality of corridor display units each associated with a facility location, the plurality of corridor display units each including a first flat panel display, a second flat panel display in an opposed arrangement to the first flat panel display, and a mounting frame adapted for mounting to a corridor surface proximate the facility location; and a display controller operatively associated with one or more of the plurality of corridor display units, the display controller programmed to generate a plurality of image files indicative of data input to the display controller, wherein the plurality of image files are for rendering a contextual annunciation image on the first and/or the second flat panel display that includes both a textual component and a graphical component associated with the data input to the display controller;

wherein the display controller is operatively associated with a logic base comprising logic rules for selection of an image file from the plurality of image files for display in the contextual annunciation image on at least one of the plurality of corridor display units;

wherein the plurality of image files comprise an image file associated with real-time data and an image file associated with prerecorded data;

wherein the logic base includes prioritization rules for selection of both the image file associated with real-time data and the image file associated with prerecorded data for inclusion in the contextual annunciation image; and wherein the display controller is further programmed to display both the image file associated with real-time data and the image file associated with the prerecorded data in the contextual annunciation image based on the prioritization rules such that the image file associated with real-time data is displayed with emphasis over the image file associated with the prerecorded data.

2. The hospital network system of claim 1, wherein the contextual annunciation image includes one or more patient status data and location status data.

3. The hospital network system of claim 2, wherein the patient status data includes one or more of real-time patient status data and prerecorded patient status data.

4. The hospital network system of claim 3, wherein the real-time patient status data originates from a caregiver call system associated with the patient location.

5. The hospital network system of claim 4, wherein the prerecorded patient status data originates from a patient electronic medical record.

6. The hospital network system of claim 1, wherein the contextual annunciation image includes location status data.

7. The hospital network system of claim 6, wherein the location status data includes one or more of real-time location status data and prerecorded location status data.

8. The hospital network system of claim 7, wherein the real-time location status data is an occupancy status of the facility.

9. The hospital network system of claim 1, further comprising a real-time location system (RTLS) including a plurality of locating tag transponders and a plurality of fixed sensors.

10. The hospital network system of claim 9, wherein the corridor display unit is configured to generate the textual component of the contextual annunciation image in a preferred language based on input from the RTLS.

11. The hospital network system of claim 1, further comprising an Assignment Scheduler system to maintain staff and caregiver assignments and the contextual annunciation image is for guiding a caregiver to the patient location.

12. The hospital network system of claim 1, further comprising one or more caregiver call devices communicatively connected with one of the plurality of corridor display units through a patient location network connector; and wherein the display controller generates the contextual annunciation image reflective of real-time patient status data received from the one or more caregiver call devices.

13. The hospital network system of claim 1, wherein the plurality of the corridor display units are communicatively connected by a corridor communication network and each of the plurality of corridor display units include a unique network address.

14. The hospital network system of claim 13, wherein the logic rules utilize the unique network address for generating the plurality of image files from data input to the display controller.

15. The hospital network system of claim 14, wherein the plurality of corridor display units operate in concert by use of the unique network addresses.

16. The hospital network system of claim 15, wherein the corridor communication network is configured to supply electrical power to the plurality of corridor display units.

17. A corridor display unit for annunciating information within a corridor of a hospital or health facility comprising:

a flat panel display for displaying a contextual annunciation image including a textual component and a graphical component;

a mounting frame for mounting the corridor display unit to a corridor surface, the mounting frame outlining and enclosing the flat panel display; and a display controller operatively associated with the corridor display unit and programmed to generate a plurality of image files for rendering the contextual annunciation image indicative of data input to the display controller;

wherein the display controller is operatively associated with a logic base comprising logic rules for selection of an image file from the plurality of image files for display in the contextual annunciation image on the flat panel display;

wherein the plurality of image files comprise an image file associated with real-time data and an image file associated with prerecorded data;

wherein the logic base includes prioritization rules for selection of both the image file associated with real-time data and the image file associated with prerecorded data for inclusion in the contextual annunciation image; and wherein the display controller displays both the image file associated with real-time data and the image file associated with the prerecorded data in the contextual annunciation image based on the prioritization rules such that the image file associated with real-time data is displayed with emphasis over the image file associated with the prerecorded data.

18. The corridor display unit of claim 17, comprising a second flat panel display arranged parallel and opposed to the first flat panel display.

19. The corridor display unit of claim 17, wherein the mounting panel is rectangular and includes four straight frame legs.

20. The corridor display unit of claim 18, wherein the mounting frame includes a mounting bracket orthogonal to a first and second visual plane of the first and second flat panel displays.

21. The corridor display unit of claim 19, wherein the mounting bracket is configured for placement adjacent the corridor surface, and the corridor surface is one of a ceiling or a wall.

22. A hospital network system comprising:

a corridor display unit including a first flat panel display, a second flat panel display in an opposed arrangement with the first flat panel display, and a mounting frame adapted for mounting to a corridor surface proximate the patient location;

a display controller networked to the corridor display unit and programmed to generate a plurality of image files corresponding to a contextual annunciation image for rendering on the flat panel display, the contextual annunciation image indicative of data input to the display controller;

one or more network servers storing patient status data and communicatively networked to the display controller to communicate the patient status data for selection and inclusion in the contextual annunciation image; and a caregiver call system including one or more call devices communicatively networked to the display controller for communicating patient status data for generating and inclusion in the contextual annunciation image;

wherein the display controller is operatively associated with a logic base comprising logic rules for selection of an image file from the plurality of image files for display in the contextual annunciation image on the flat panel display;

wherein the plurality of image files comprise an image file associated with real-time data and an image file associated with prerecorded data;

wherein the logic base includes prioritization rules for selection of both the image file associated with real-time data and the image file associated with prerecorded data for inclusion in the contextual annunciation image; and wherein the display controller displays both the image file associated with real-time data and the image file associated with the prerecorded data in the contextual annunciation image based on the prioritization rules such that the image file associated with real-time data is displayed with emphasis over the image file associated with the prerecorded data.

* * * * *